(12) United States Patent
Drott et al.

(10) Patent No.: US 7,836,914 B2
(45) Date of Patent: Nov. 23, 2010

(54) SWITCHING DEVICE AND APPARATUS FOR CONTROLLING FLOW OF A FLUID

(75) Inventors: Johan Drott, Bjärred (SE); Eddie Nils-Joel Nilsson, Sosdala (SE)

(73) Assignee: Gambro Lundia AB (SE)

(*) Notice: Subject to any disclaimer, the term of this patent is extended or adjusted under 35 U.S.C. 154(b) by 1747 days.

(21) Appl. No.: 11/008,195

(22) Filed: Dec. 10, 2004

(65) Prior Publication Data

US 2005/0131335 A1 Jun. 16, 2005

Related U.S. Application Data

(60) Provisional application No. 60/528,727, filed on Dec. 11, 2003, provisional application No. 60/530,511, filed on Dec. 17, 2003.

(51) Int. Cl.
*A61M 37/00* (2006.01)
(52) U.S. Cl. .............. 137/625.47; 251/7; 251/297; 604/6.1
(58) Field of Classification Search ............ 137/625.43; 251/7, 297; 604/6.1
See application file for complete search history.

(56) References Cited

U.S. PATENT DOCUMENTS

| 2,709,785 | A | | 5/1955 | Fielden et al. |
|---|---|---|---|---|
| 3,324,720 | A | | 6/1967 | Sutherland |
| 3,332,439 | A | * | 7/1967 | Burke ............... 137/556 |
| 3,396,331 | A | | 8/1968 | Sperry, III |
| 3,404,336 | A | | 10/1968 | Rosenthal |
| 3,433,935 | A | | 3/1969 | Sheman |
| 3,446,073 | A | | 5/1969 | Auphan et al. |
| 3,450,984 | A | | 6/1969 | Holmes |
| 3,482,575 | A | | 12/1969 | Claff et al. |
| 3,491,592 | A | | 1/1970 | Evers et al. |
| 3,545,428 | A | | 12/1970 | Webster, Jr. |
| 3,561,266 | A | | 2/1971 | Auphan et al. |
| 3,604,263 | A | | 9/1971 | Auphan et al. |
| 3,619,423 | A | | 11/1971 | Galletti et al. |

(Continued)

FOREIGN PATENT DOCUMENTS

DE 4024434 2/1992

(Continued)

OTHER PUBLICATIONS

Hester et al, "A New Technique for Determining Recirculation n the ESRD Patient," *Nephrology News & Issues*, pp. 44-55 (1993).

(Continued)

*Primary Examiner*—John Fox
(74) *Attorney, Agent, or Firm*—Finnegan, Henderson, Farabow, Garrett & Dunner, LLP

(57) ABSTRACT

A switching device for a fluid distribution set presenting a deformable portion having a first port, a second port, a third port and a fourth port, is disclosed. The switching device comprises an active portion adapted, in use, for clamping the deformable portion of the fluid distribution set, and a housing body defining a seat for receiving the deformable portion. The switching device can be operated according to first and second clamping positions, wherein the active portion is approached to a corresponding active surface of the housing body. A fluid control apparatus comprising the above switching device and the portion of the fluid distribution set is also described.

39 Claims, 9 Drawing Sheets

U.S. PATENT DOCUMENTS

| | | | |
|---|---|---|---|
| 3,640,271 A | 2/1972 | Horton | |
| 3,722,276 A | 3/1973 | Chandler et al. | |
| 3,733,899 A | 5/1973 | Auphan et al. | |
| 3,867,688 A | 2/1975 | Koski | |
| 3,964,479 A | 6/1976 | Boag et al. | |
| 3,980,946 A | 9/1976 | Fleury | |
| 3,985,134 A | 10/1976 | Lissot et al. | |
| 3,987,788 A | 10/1976 | Emil | |
| 4,037,817 A * | 7/1977 | Chernak | 251/7 |
| 4,081,372 A | 3/1978 | Atkin et al. | |
| 4,136,563 A | 1/1979 | Mueller et al. | |
| 4,138,639 A | 2/1979 | Hutchins | |
| 4,153,418 A | 5/1979 | Haas | |
| 4,167,870 A | 9/1979 | Haas | |
| 4,181,610 A | 1/1980 | Shintani et al. | |
| 4,361,049 A | 11/1982 | Volgyesi | |
| 4,391,124 A | 7/1983 | Drost et al. | |
| 4,432,231 A | 2/1984 | Napp et al. | |
| 4,434,648 A | 3/1984 | Drost et al. | |
| 4,446,871 A | 5/1984 | Imura | |
| 4,508,622 A | 4/1985 | Polaschegg et al. | |
| 4,650,458 A | 3/1987 | Dahlberg et al. | |
| 4,715,849 A | 12/1987 | Gion et al. | |
| 4,738,265 A * | 4/1988 | Ritchart et al. | 600/486 |
| 4,739,492 A | 4/1988 | Cochran | |
| 4,740,755 A | 4/1988 | Ogawa | |
| 4,777,938 A | 10/1988 | Sirota | |
| 4,797,655 A | 1/1989 | Orndal et al. | |
| 4,821,996 A | 4/1989 | Bellotti et al. | |
| 4,822,341 A | 4/1989 | Colone | |
| 4,825,168 A | 4/1989 | Ogawa et al. | |
| 4,856,321 A | 8/1989 | Smalling et al. | |
| 4,885,001 A | 12/1989 | Leppert | |
| 4,885,087 A | 12/1989 | Kopf | |
| 4,923,598 A | 5/1990 | Schäl | |
| 4,995,268 A | 2/1991 | Ash et al. | |
| 5,004,459 A | 4/1991 | Peabody et al. | |
| 5,024,756 A | 6/1991 | Sternby | |
| 5,058,416 A | 10/1991 | Engelhardt et al. | |
| 5,082,025 A | 1/1992 | Devries et al. | |
| 5,092,836 A | 3/1992 | Polaschegg | |
| 5,098,373 A | 3/1992 | Polaschegg | |
| 5,100,554 A | 3/1992 | Polaschegg | |
| 5,190,071 A * | 3/1993 | Sule | 137/595 |
| 5,230,341 A | 7/1993 | Polaschegg | |
| 5,312,550 A | 5/1994 | Hester | |
| 5,357,967 A | 10/1994 | Dixon et al. | |
| 5,372,136 A | 12/1994 | Steuer et al. | |
| 5,442,969 A | 8/1995 | Troutner et al. | |
| 5,453,576 A | 9/1995 | Krivitski | |
| 5,474,276 A * | 12/1995 | Steinbock et al. | 251/4 |
| 5,507,723 A | 4/1996 | Keshaviah | |
| 5,510,716 A | 4/1996 | Buffaloe, IV et al. | |
| 5,510,717 A | 4/1996 | Buffaloe, IV et al. | |
| 5,518,623 A | 5/1996 | Keshaviah et al. | |
| 5,570,026 A | 10/1996 | Buffaloe, IV et al. | |
| 5,588,959 A | 12/1996 | Ahmad et al. | |
| 5,595,182 A | 1/1997 | Krivitski | |
| 5,605,630 A | 2/1997 | Shibata | |
| 5,644,240 A | 7/1997 | Brugger | |
| 5,662,806 A | 9/1997 | Keshaviah et al. | |
| 5,685,988 A | 11/1997 | Malchesky | |
| 5,685,989 A | 11/1997 | Krivitski et al. | |
| 5,771,914 A * | 6/1998 | Ling et al. | 137/1 |
| 5,830,365 A | 11/1998 | Schneditz | |
| 5,866,015 A | 2/1999 | Krämer | |
| 5,894,011 A | 4/1999 | Prosl et al. | |
| 5,900,726 A | 5/1999 | Brugger et al. | |
| 5,902,253 A | 5/1999 | Pfeiffer et al. | |
| 6,061,590 A | 5/2000 | Krivitski | |
| 6,117,099 A | 9/2000 | Steuer et al. | |
| 6,153,109 A | 11/2000 | Krivitski | |
| 6,177,049 B1 | 1/2001 | Schnell et al. | |
| 6,189,388 B1 | 2/2001 | Cole et al. | |
| 6,210,591 B1 | 4/2001 | Krivitski | |
| 6,308,737 B1 * | 10/2001 | Krivitski | 137/597 |
| 6,319,465 B1 | 11/2001 | Schnell et al. | |
| 6,514,419 B2 | 2/2003 | Krivitski | |
| 6,596,234 B1 | 7/2003 | Schnell et al. | |
| 6,623,443 B1 | 9/2003 | Polaschegg | |
| 6,695,807 B2 * | 2/2004 | Bell et al. | 604/6.16 |
| 2001/0031222 A1 | 10/2001 | Schnell et al. | |
| 2001/0050256 A1 | 12/2001 | Krivitski | |
| 2003/0018290 A1 * | 1/2003 | Brugger et al. | 604/6.1 |
| 2003/0138348 A1 | 7/2003 | Bell et al. | |

FOREIGN PATENT DOCUMENTS

| | | |
|---|---|---|
| DE | 19537688 | 5/1996 |
| DE | 19528907 | 11/1996 |
| DE | 19541783 | 3/1997 |
| DE | 19901078 | 2/2000 |
| EP | 0 018 817 A1 | 11/1980 |
| EP | 0097366 | 1/1984 |
| EP | 0 089 003 B1 | 11/1987 |
| EP | 0272414 | 6/1988 |
| EP | 0 693 296 A1 | 1/1996 |
| EP | 0 693 297 A1 | 1/1996 |
| EP | 0773035 | 5/1997 |
| EP | 0 835 669 A2 | 4/1998 |
| EP | 0845273 | 6/1998 |
| EP | 0 590 810 B1 | 7/1998 |
| EP | 0900094 | 3/1999 |
| EP | 0 928 614 A1 | 7/1999 |
| EP | 0943369 | 9/1999 |
| EP | 1044695 | 10/2000 |
| EP | 1 106 191 A | 6/2001 |
| EP | 1 106 191 A1 | 6/2001 |
| ES | 2026508 T | 5/1992 |
| GB | 2093192 | 8/1982 |
| JP | 60190873 | 9/1985 |
| JP | 5236990 | 9/1993 |
| RU | 521891 | 10/1976 |
| RU | 1013853 A | 4/1983 |
| WO | WO-96/08305 | 3/1996 |
| WO | WO-97/01289 | 1/1997 |
| WO | WO-97/10013 | 3/1997 |
| WO | WO-98/17193 | 4/1998 |
| WO | WO-98/17334 | 4/1998 |
| WO | WO-98/32477 | 7/1998 |
| WO | WO-99/64088 | 12/1999 |
| WO | WO-00/18451 | 4/2000 |
| WO | WO-00/74732 A1 | 12/2000 |

OTHER PUBLICATIONS

Petitclerc et al., "A Model for Non-invasive Estimation of in vivo Dialyzer Performances and Patient's Conductivity During Hemodialysis," *The International Journal of Artificial Organs*, vol. 16, No. 8, pp. 585-591 (1993).

Petitclerc et al., "Non-invasive Monitoring of Effective Dialysis Dose Delivered to the Haemodialysis Patient," *Nephrol. Dial. Transplant*, vol. 10, pp. 212-216 (1995).

Mercadal et al., "Determination of Access Blood Flow from Ionic Dialysance: Theory and Validation," *Kidney International*, vol. 56, pp. 1560-1565 (1999).

Gambro, "FAM 10 Fistula Flow Studies and Their Interpretation," pp. 1-31 (on or before 1991).

Salamon et al., "A Low Frequency Electrodeless Conductometer for Measuring the Electrical Conductivity of Solutions," *Industrial Group Headquarters*, translation from *Chemicky Prumysl*, vol. 6/31, pp. 10-14 (1956).

Sherman, "Recirculation Revisited," *Seminars in Dialysis*, vol. 4, No. 4, pp. 221-223 (1991).

Smith et al., "Cardiac Output Determined by the Saline Conductivity Method Using an Extra-arterial Conductivity Cell," *Cardiovascular Research Center Bulletin*, vol. 5, No. 4, pp. 123-134 (1967).

Thomsen et al., "Evaluation of Clinical Examination Preceding Surgical Treatment of AV-Fistula Problems," *Acta Chir Scand*, vol. 151, pp. 133-137 (1985).

Transonic Systems Inc., "Access Flow & Recirculation Measured During Hemodialysis," (1994).

Aldridge et al., "The Assessment of Arteriovenous Fistulae Created for Haemodialysis from Pressure and Thermal Dilution Measurements," *Journal of Medical Engineering & Technology*, vol. 8, No. 3, pp. 118-124 (1984).

Aldridge et al., "Instrument Design for the Bedside Assessment of Arteriovenous Fistulae in Haemodialysis Patients," *Proc EDTNA-ERCA*, vol. 14, pp. 255-260 (1985).

Carr, "Integration of Decaying Exponential Sensor Output Signals," *SENSORS*, pp. 28-34 (1989).

Daugirdas et al., "The Fourth Annual Advanced Dialysis Technical Symposium, Jun. 10, 1988," *Dialysis & Transplantation*, vol. 17, No. 8, pp. 432-433 (1988).

Fresenius Dialysetechnik, "BTM 4008 Fistelrezirkulation," (1993).

Gambro, "Fistula Assessment Monitor FAM 10," (aprx. 1985).

Gambro, "Fistula Assessment Monitor FAM 10, Operator's Manual," (aprx. 1985).

Gambro, "Fistula Assessment Monitor FAM 10, Service Manual," (aprx. 1985).

Gani et al., "Use of the Fistula Assessment Monitor to Detect Stenoses in Access Fistulae," *American Journal of Kidney Diseases*, vol. XVII, No. 3, pp. 303-306 (1991).

Greenwood et al., "Assessment of Arteriovenous Fistulas from Pressure and Recirculation Studies, Clinical Experience in 215 Upper Limb Fistulas," *Proc EDTA-ERA*, vol. 22, pp. 296-302 (1985).

Greenwood et al., "Assessment of Arteriovenous Fistulas from Pressure and Thermal Dilution Studies: Clinical Experience in Forearm Fistulae," *Clinical Nephrology*, vol. 23, No. 4, pp. 189-197 (1985).

Goldstein et al., "The Assessment of Arteriovenous Fistulae from Pressure and Recirculation Studies," *Proc EDTNA-ERCA*, vol. 14, pp. 207-215 (1985).

Hart et al., "A Noninvasive Electromagnetic Conductivity Sensor for Biomedical Applications," *IEEE Transactions on Biomedical Engineering*, vol. 35, No. 12, pp. 1011-1019 (1988).

Hester et al., "The Determination of Hemodialysis Blood Recirculation Using Blood Urea Nitrogen Measurements," *American Journal of Kidney Diseases*, vol. XX, No. 6, pp. 598-602 (1992).

Kramer et al., "Automated Measurement of Recirculation," *EDTNA-ERCA Journal*, vol. XIX, No. 2, pp. 6-9 (1993).

Kramer et al., "A Device for Control of Thermal Parameters and Recirculation Measurement in Hemodialysis," *Fourth Annual British Renal Symposium*, poster (1992).

"Transonic® Hemodialysis Monitor Measures Access Flow Recirculation Cardiac Output Routinely during Dialysis," *Transonic System, Inc.* brochure, ASAIO (1995).

Krivitski, "Novel Method to Measure Access Flow during Hemodialysis by Ultrasound Velocity Dilution Technique," *ASAIO Journal*, vol. 41, pp. M741-M745 (1995).

Depner et al., "Clinical Measurement of Blood Flow in Hemodialysis Access Fistulae and Grafts by Ultrasound Dilution," *ASAIO Journal*, vol. 41, pp. M745-M749 (1995).

Depner et al., "Hemodialysis Access Recirculation Measured by Ultrasound Dilution," *ASAIO Journal*, vol. 41, pp. M749-753 (1995).

Krivitski, "Theory and Validation of Access Flow Measurement by Dilution Technique During Hemodialysis," *Kidney International*, vol. 48, pp. 244-250 (1995).

Krivitski, "Accuracy of Ultrasound Dilution Method to Measure Access Flow (AF) in Hemodialysis," *XIIIth International Congress of Nephrology*, Abstract (1995).

Krivitski, "New Method to Measure Recirculation (Rc) and Access Flow During Hemodialysis (HD)," *American Nephrology Nurses' Association 26th National Symposium Exhibitor Continuing Education Program*, Abstract (1996).

Depner, "Changes in Access Blood Flow (Qac) and Appearance of Recirculation (RC) During Hemodialysis," *XIIIth International Congress of Nephrology*, Abstract (1995).

Depner et al., "Hemodialysis Access Recirculation (Rc) Measured by Ultrasound Dilution," *ASAIO Journal*, vol. 41, No. 1, p. 80 (1995).

Depner et al., "Clinical Measurement of Blood Flow in Hemodialysis Access Fistulae and Grafts by Ultrasound Dilution," *ASAIO Journal*, vol. 41, No. 1, p. 80 (1995).

Transonic Systems, Inc., "Recirculation, Access Flow Measurements," brochure, pp. 19-26 (1995).

Krivitski, "Cardiac Output Measurement in Extracorporal Systems by Ultrasound Velocity Dilution," *ASAIO Journal*, American Society of Internal Organs, 40th Anniversary Meeting, 1994 Abstracts, Abstract, p. 82 (1994).

Sands, et al., "The Effect of Doppler Flow Screening Studies and Elective Revisions on Dialysis Access Failure," *ASAIO Journal*, pp. M524-M527 (1992).

Nosher, "Death, Taxes, and Vascular Access Dysfunction," *Seminars in Dialysis*, vol. 4, No. 2, pp. 67-68 (1991).

In-Line Diagnostics, "Improve the Clinical Outcome of Every Patient with Crit-Line: The World's Only Non-Invasive Hct/ABV Monitor," brochure, 4 pgs. (undated).

In-Line Diagnostics, "Noninvasive Blood Volume Monitoring Blood Volume Profile," brochure, 2 pgs. (1994).

Bower et al., "Circulatory Function During Chronic Hemodialysis," *Trans. Amer. Soc. Artif. Int. Organs*, vol. XV, pp. 373-377 (1969).

Aldridge, "The Use and Management of Arteriovenous Fistulae Fact and Fiction," *EDTNA-ERCA Journal*, Vol. XVII, No. 4, pp. 29-35 (1991).

Hester et al., "Non-invasive Determination of Recirculation in the Patient on Dialysis," *ASAIO Journal*, pp. M190-M193 (1992).

Hester et al., "Non-invasive Measurement of Recirculation in the Dialysis Patient," *Abstract No. 7* (1992).

Greenwood et al., "Single Needle Dialysis," *Journal of Medical Engineering & Technology*, vol. 6, No. 3, pp. 93-98 (1982).

Konner et al., "Transvenous Serial Xero-arteriography: A New Non-invasive angiographic method for AV-fistulas in Haemodialysis Patients," *Proc EDTA*, vol. 18, pp. 305-309 (1981).

Forsberg et al., "Quantitative Doppler and Ultrasound Measurements in Surgically Performed Arteriovenous Fistulas of the Arm," *Acta Radiologica Diagnosis 21*, Fasc. 6, pp. 769-771 (1980).

Schneditz et al., "Cardiopulmonary Recirculation in Dialysis, An Underrecognized Phenomenon," *ASAIO Journal*, pp. M194-M196 (1992).

Guyton, "The Indicator Dilution Method," *Textbook of Medical Physiology*, pp. 287-288 (1991).

Gothlin et al., "A Dye-dilution Method for the Determination of Blood Flow in Cimino-brescia Arteriovenous Fistulae," *Investigative Urology*, pp. 167-168 (1977).

Oudenhoven et al., "Magnetic Resonance, a New Method for Measuring Blood Flow in Hemodialysis Fistulae," *Kidney International*, No. 45, pp. 884-889 (1994).

Rocha et al., "Arteriovenous Shunt Measured by Bolus Dye Dilution: Reproducibility and Comparison Between Two Injection Sites," *Catheterization and Cardiovascular Diagnosis*, vol. 11, pp. 473-481 (1985).

Gottlieb et al., "Radiotracer Method for Nonsurgical Measurement of Blood Flow in Bovine Graft Arteriovenous Fistulas," *Proc. Dialysis Transplant Forum*, pp. 107-108 (1976).

Lantz et al., "Determination of Blood Flow Through Arteriovenous Fistulae and Shunts," *Acta Radiologica Diagnosis 20*, vol. 5, pp. 727-736 (1979).

Depner et al., "Access Flow Measured from Recirculation of Urea During Hemodialysis with Reversed Blood Lines," JASN, Abstract, vol. 6, No. 3, p. 486.

Lindsay et al., "Monitoring Vascular Access Flow," *Advances in Renal Replacement Therapy*, vol. 6, No. 3, pp. 273-277 (1999).

Lindsay et al., "Estimation of Hemodialysis Access Blood Flow Rates by a Urea Method is a Poor Predictor of Access Outcome," *ASAIO Journal*, vol. 44, pp. 818-822 (1998).

Sternby, "Urea Sensors—A World of Possibilities," *Advances in Renal Replacement Therapy*, vol. 6, No. 3, pp. 265-272 (1999).

Yarar et al., "Ultrafiltration Method for Measuring Vascular Access Flow Rates During Hemodialysis," *Kidney International*, vol. 56, pp. 1129-1135 (1999).

P.G. Sakiewicz. et al., "Introduction of a Switch that Can Reverse Blood Flow Direction On-Line During Hemodialysis," *ASAIO Journal*, vol. 46, n. 4, Jul. 2000, pp. 464-468.

R.N. Greenwood, et al. "Serial Blood Water Estimations and In-Line Blood Viscometry: The Continuous Measurement of Blood Volume During Dialysis Procedures," Clinical Science (1984) 66, pp. 575-583.

International Search Report for International Application No. PCT/IB2004/003783.

J.S. Gani et al., "Use of the Fistula Assessment Monitor to Detect Stenoses in Access Fistulae," (ABSTRACT) Australian Society of Nephrology, 1989, Australia.

L. Goldstein, "Assessment of Arteriovenous Fistulae From Pressure and Recirculation Studies," Abstract, p. 106, 1985, London, UK.

\* cited by examiner

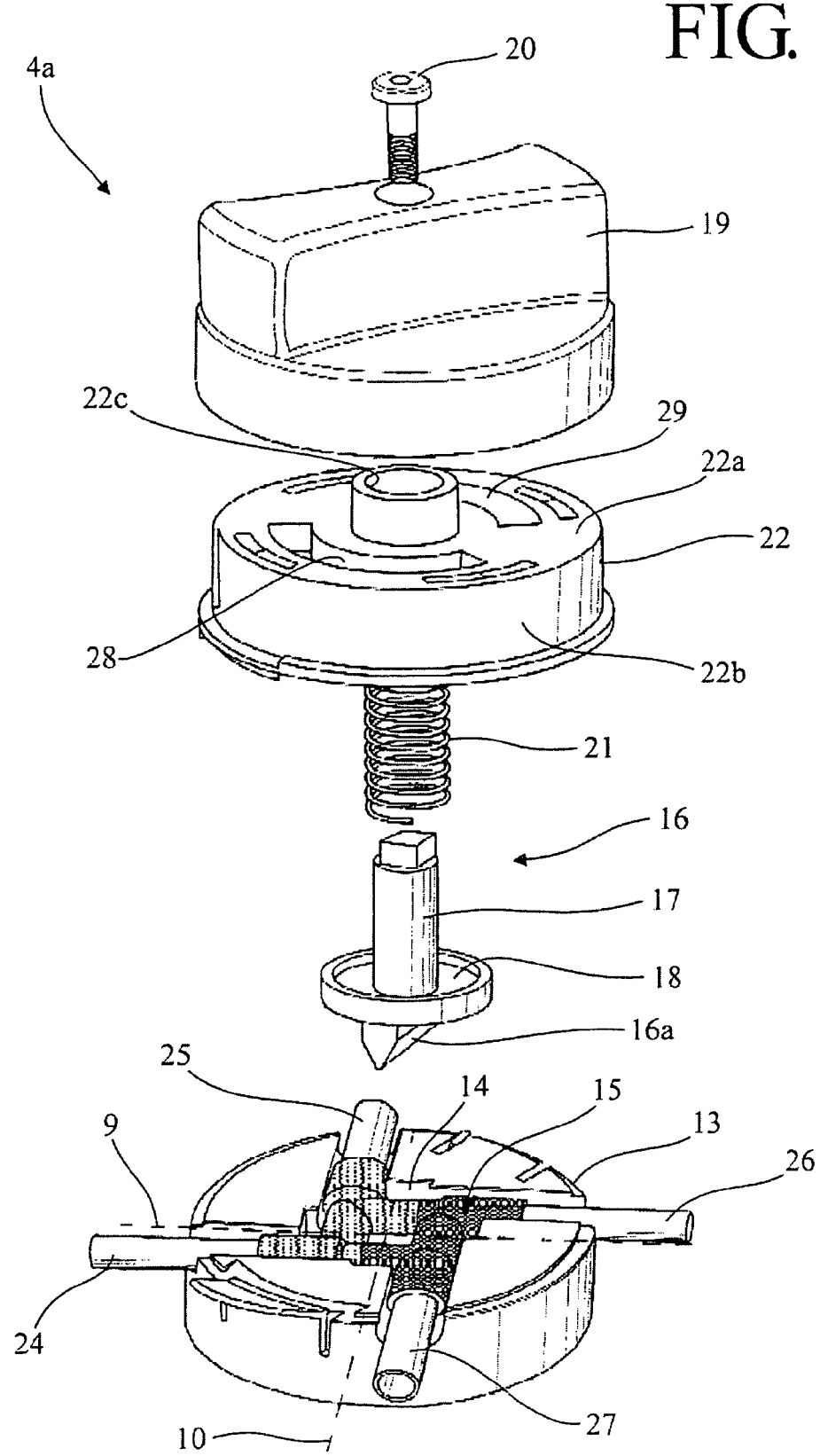

SWITCHING DEVICE AND APPARATUS FOR CONTROLLING FLOW OF A FLUID

CROSS REFERENCE TO RELATED APPLICATIONS

This application claims the benefit of U.S. Provisional Application No. 60/528,727, filed on Dec. 11, 2003 and U.S. Provisional Application No. 60/530,511, filed on Dec. 17, 2003, the contents of which are incorporated herein by reference.

TECHNICAL BACKGROUND

The present invention relates to a switching device for a fluid distribution set and to an apparatus for controlling flow of a fluid using said switching device. The invention may find application for controlling flow of a liquid in a portion of a fluid circuit comprising deformable tubing and/or deformable chambers. By way of non-limiting example, the invention may be used for controlling blood flow in an extracorporeal circuit of a blood treatment machine.

BACKGROUND OF THE INVENTION

In medicine there are many applications requiring the control of the flow of fluids such as for instance of biological fluids. One such application, which is herein referred to by way of example, is the control of the blood flow during an extracorporeal blood treatment. It is known that a conventional extracorporeal circuit comprises an arterial line, withdrawing blood from the patient, a blood treatment unit, and a venous line which returns treated blood to the patient. In order to withdraw blood from a patient, a blood access is commonly created in the nature of an arterio-venous shunt, referred to as a fistula. During the blood treatment, blood is taken out from the fistula at an upstream position of the fistula and is returned to the fistula at a downstream position. As the efficacy of the treatment is influenced by the actual flow through the fistula and by the proper working of the accesses, it is of interest studying and monitoring fistula parameters. Therefore during the years several methods for monitoring fistula parameters have been developed. According to some of these methods it is necessary to reverse blood flow in part of the extracorporeal circuit so that blood is taken out from the fistula at a downstream position and blood is returned to the fistula at an upstream position, while keeping the same sense of flow in the treatment unit. A number of methods and devices are known for reversing the flow of blood.

EP5605630 relates to a switching mechanism on bloodline and on dialysis circuit. The bloodline switching mechanism according to this reference changes the direction of the blood flow through the dialyzer and therefore undesirably affects the blood treatment.

It is also known in the art the use of true valves, with a rotating body having channels, which can be aligned or misaligned with respective ports for creating the desired flow switching as in U.S. Pat. No. 5,894,011, in U.S. 2001/0031222, in U.S. Pat. No. 6,319,465B1, or in U.S. Pat. No. 6,177,049 (EP1083947). More in detail, U.S. Pat. No. 5,894,011 relates to a device for selectively controlling the direction of blood flow to and from the patient during hemodialysis and comprises two interlocking disks that rotate in relation to each other without separating. The two disks have fluid fittings that allow the bloodlines attached to the patient to connect to one of the disks and the blood inlet and outlet for the hemodialysis machine to connect to the other. The center of each fluid fitting is a channel that aligns to a corresponding channel in the other disk. The disks rotate between two fixed relative positions, referred to herein as preferred alignments. The preferred alignments are such that the line drawing blood from the patient in the first preferred alignment becomes the line returning blood to the patient in the second preferred alignment, and the line returning blood to the patient in the first preferred alignment becomes the line drawing blood from the patient in the second preferred alignment.

U.S. 2001/0031222 relates to a kit comprising a tube set, instructions and a packaging. The instructions detail how to use the tube set which includes a flow reversal valve.

U.S. Pat. No. 6,319,465B1 relates to a tubular set is provided for use with extracorporeal treatment of blood. The set comprises: a flow reversing valve having a patient arterial line and a patient venous line each separately connected to one side of the valve. A unit arterial line and a unit venous line are each separately connected to the other side of the valve. The patient arterial line connects with the unit arterial line in a first position of a valve, and the patient venous line connects with the unit venous line in the same first valve position. The patient arterial line connects with the patient venous line in a second position of a valve, while the patient venous line connects with the unit arterial line in the same second valve position.

U.S. Pat. No. 6,177,049 (EP1083947) refers to a tubular set provided for the extracorporeal treatment of blood. The set comprises a patient arterial line and a patient venous line, each line having a patient connector at one end thereof. Each patient line connects at its other end to a reversing flow valve. The valve also connects to respective first ends of a blood processing unit arterial line and a blood processing unit venous line. Each of the unit lines carry a connector at ends opposed to the first ends for connection respectively to arterial and venous ports of a blood processing device, typically a dialyzer. The reversing flow valve has a first position that respectively connects the patient and unit arterial lines with the patient and unit venous lines. The reversing flow valve has a second position that connects the patient arterial line with the unit venous line, and the unit arterial line with the patient venous line. Thus, blood flow between the two patient lines can be reversed without reversing flow through the two unit lines and the connected dialyzer. Problems common to the above devices having rotating bodies in direct contact with blood are:

risk that the blood clogs in the space between the two rotatably connected parts;
 risk that blood cells may be damaged during rotation of the rotatably connected parts. Many patients who are dependent on dialysis also have a low production of blood cells. Thus, it is important to avoid damaging blood cells during dialysis.

Moreover notice that all the above devices imply a relatively complicated and, as such, expensive structure for a product which is entirely disposable.

An alternative solution is shown in U.S. Pat. No. 6,308,737, which relates to a diverter for selectively providing fluid communication between ports to a common chamber. The diverter includes a deformable common chamber having a plurality of ports. Upon deforming the common chamber along a given line, fluid communication between selected ports is precluded, which flow preclusion is used to effectively reverse a flow direction in a circuit connected to the diverter.

The above disclosed device lacks an efficient, perfectly controlled and easy way for deforming the chamber.

Moreover, it would be desirable to avoid any risk of uncontrolled flow of biological fluid between the different ports.

Further it is in many instances advantageous to be able to automate the flow control device.

A further blood flow reversing system is shown in U.S. 2003/0138348 and comprises a quadrilateral tubing structure with four ports connectable to the arterial and venous lines. In use, two tube portions of the reversing system are each designed to be put along the respective venous or arterial line, while two other tube portions are designed to transversely cross the arterial and venous line. A clamp can squeeze the pairs of the above tube portion in order to achieve a normal configuration or a reversed configuration.

Also this reversing system though easy to operate does not provide the user with a quick and accurate tool to switch the configuration of the lines. The clamping action is not able to give a substantially simultaneous repeatable and effective action through all the clamping area. The switching operation is not difficult but cannot be done quickly and precisely as desirable for certain applications.

Publication "Determination of access blood flow from ionic dialysance: theory and validation", Mercadal et al., Kidney international, vol. 56 (1999), pages 1560-1565, shows a flow reversing device comprising four tube portions which can be properly clamped in order to put the blood lines either in the normal or in the reversed configuration.

Also this solution has the same drawbacks of U.S. 2003/0138348.

It would therefore be advantageous to provide a device that fulfils the requirements for valves for biological fluid in an alternative way. It would also be advantageous to simultaneously avoid at least some of the problems stated above.

EP1106191 shows a peritoneal dialysis switch valve, wherein a rotating body with cams clamps tube portions and creates a switching mechanism which is acting on a T shaped tubing and not suitable for use in a four ports deformable structure for veiculating fluid.

SUMMARY OF THE INVENTION

An object of the present invention is to provide a switching device and apparatus for controlling flow of fluid among four different ports, which device and apparatus solve at least one of the problems stated above.

Another object of the present invention is to provide an easy to operate switching device and apparatus for controlling flow of fluid able to be quickly activated and able to quickly provide switching from one configuration to the other.

A further object of the present invention is to provide a switching device and apparatus for controlling flow of fluid among four different ports, which device and apparatus only allow flow of fluid between pairs of ports.

Still another object of the present invention is to provide a switching device and apparatus for controlling flow of fluid among four different ports, which device and apparatus may be easily automated.

Furthermore an object of the invention is to provide a switching device and an apparatus using said device, which can effectively and accurately clamp a prescribed region of a deformable tubing or chamber to thereby achieving an effective switching of the configuration.

Finally it is an auxiliary object of the invention a device capable of stably keep prescribed clamping conditions unless operated to move away from said positions.

At least one of these objects is attained by a switching device for a fluid distribution set, said set presenting an at least partially deformable portion having a first port, a second port, a third port and a fourth port, the switching device comprising clamping means having at least an active portion adapted, in use, for clamping said at least partially deformable portion of the fluid distribution set, characterized in that the device also comprises a housing body defining a seat for receiving said at least partially deformable portion, the clamping means being coupled with the housing body and being positionable according to at least a first and a second clamping positions, wherein the active portion is approached to a corresponding active surface of the same housing body.

By having the clamping means cooperating with an housing to clamp the portion, then there is no risk that the clamp means clamps in an incorrect position. Further, the device is easily operated.

Preferably the clamp means is arranged to clamp over the entire clamp area substantially simultaneously.

As the clamp means is arranged to clamp over the entire clamp area substantially simultaneously there is no risk for flow of fluid along uncontrolled paths.

The clamp means may comprise a number of movable parts. However, according to some embodiments the clamp means comprises only one part movable in relation to the housing. Such a device is more easily implemented than a device comprising a number of movable parts.

The device can also comprise means for allowing the clamping means to clamp the deformable portion in said positions only.

The device may comprise urging means for forcing the clamp means towards a housing wall. The urging means may be a resilient means, such as a spring, or means of other nature (for instance magnetic means) able to generate a force directing the active portion against the a wall portion. There are a number of different alternatives for the implementation of the resilient means. The resilient means may be, e.g., a gas cylinder, a spring or other.

Also the magnetic means can include use of permanent magnets, or of magnetically chargeable bodies or of electromagnets.

As the housing is formed by a first and a second element the device may be separated in order to allow the at least partially deformable portion to be inserted into the device. In the embodiment where the urging means are associated to the second element and the at least partially deformable portion substantially positioned in a seat defined by the first element of the housing, then any opening, closing of the device and positioning of portion is really easy. In order to prevent separation of the first element and the second element by the force from the resilient means, when it forces the clamping means towards the first element, the first and second elements may be connected.

Alternatively the resilient means may of course be arranged to act between the clamping means and the first element so that the clamping means pulls the clamping means towards the first element.

The clamping means may be arranged on an axle, which is arranged in a through going hole in the second element perpendicular to the first element. By having it arranged in such a way it is easily maneuverable from the opposite side of the first element.

The device may comprise control means for steering the clamp means to be positionable for deforming the flow means, in said clamping positions only. In addition to the control means the device may also comprise return means for moving the clamp means in a preferred of said clamping positions.

The clamp means may be positionable at positions separated by approximately 90 degrees. The optimum angle for the active portion 16a depends on the form of the deformable portion 15. By having the positions substantially perpendicular to each other it is easy to implement the device.

The clamp means may be arranged to freely rotate. However, the clamp means may alternatively be positionable in two positions only. By having the clamp means positionable in two positions only it is easier to achieve secure operation of the device.

An automatic actuator can be arranged to turn the knob or the axle and, if desired, to also achieve the axial displacement of the same axle from the claming to the rest positions and vice-versa.

A device according to the present invention may be used in a number of applications. One primary use of a device according to the invention is, however, to control flow of blood.

Another example of primarily intended use is for changing the flow direction of blood during hemodialysis.

It goes without saying that the different features above may be combined in the same embodiment.

In the following different embodiments of the present invention will be described with reference to the drawings.

SHORT DESCRIPTION OF THE DRAWINGS

FIG. 2 shows an exploded view of a switching device according to the present invention.

DESCRIPTION OF PREFERRED EMBODIMENTS

With reference to the enclosed exemplifying drawing tables, a blood treatment equipment as well as several embodiments of a switching device and of an apparatus including said switching device are shown.

Figure 1:
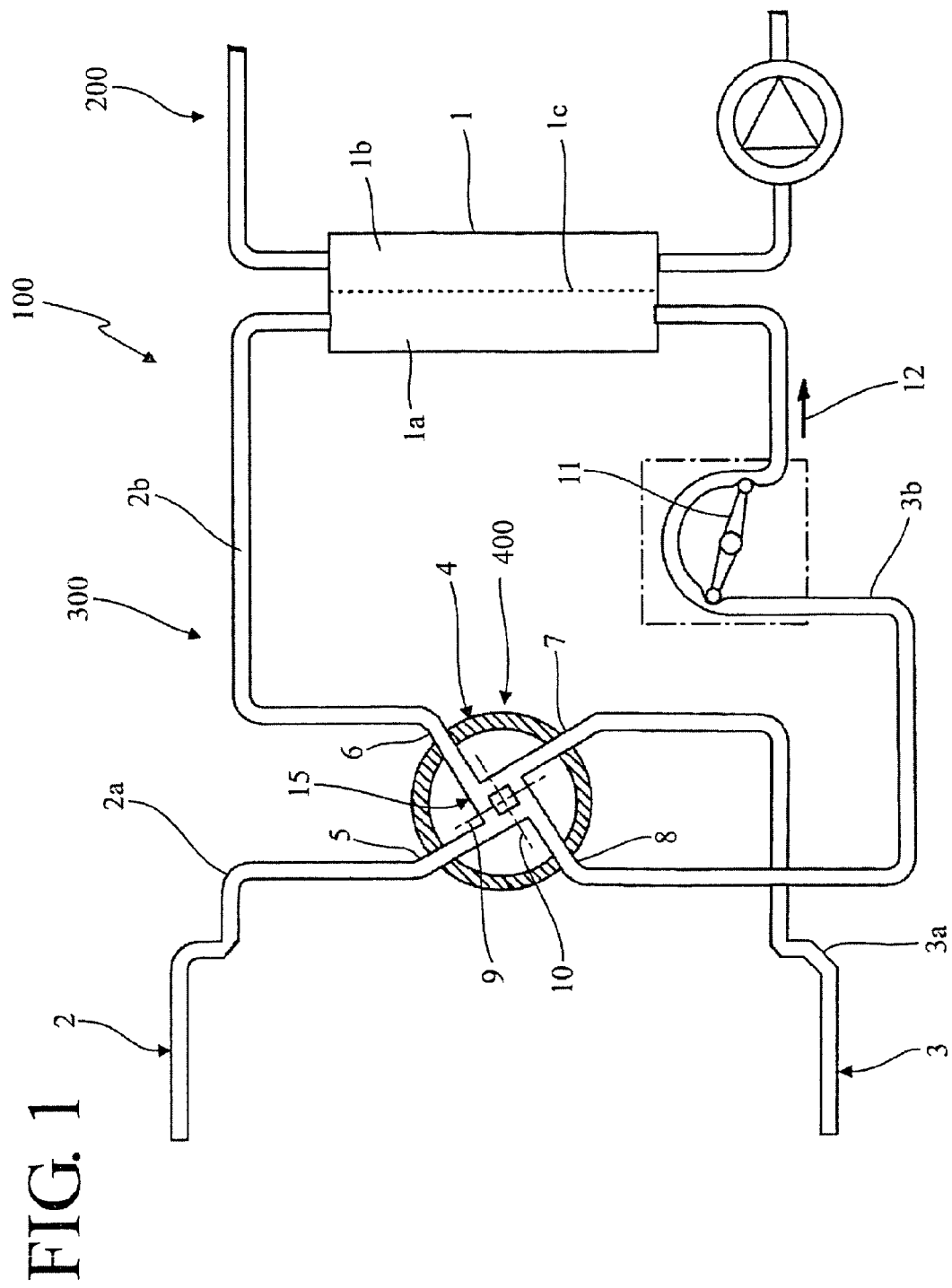
FIG. 1 shows a device and an apparatus according to the invention connected between a patient and a dialysis machine.

In detail, FIG. 1 shows a blood treatment equipment 100. The blood treatment equipment includes a section 200 (not further described in detail) adapted to prepare fresh treatment liquids and also adapted to evacuate waste liquid. The blood treatment equipment also comprises a fluid distribution set globally indicated with reference numeral 300 in the enclosed drawings. The fluid distribution set 300 presents a blood tratment unit 1 having a first and a second chamber 1a, 1b separated by a semipermeable membrane 1c, and a first and a second line 2, 3 connected to the treatment unit first chamber.

FIG. 1 shows schematically a fluid distribution set 100 comprising a blood treatment unit or filter 1. The treatment unit of FIG. 1 is a dialyzer, though said treatment unit could have been any other suitable unit such as a hemofilter, or a hemodiafilter, or an ultrafilter, or a plasmafilter or other, according to the specific treatment to be applied on the extracorporeal blood. The second chamber 1b of the unit 1 in FIG. 1 is connected, at its inlet, to a supply line of fresh dialysis liquid and, at its outlet, to a waste line for discharging used dialysis liquid.

The distribution set includes one (though two or more are not excluded in principle) at least partially deformable portion 15 connected with the first and second lines 2, 3. As it will appear clear the portion 15 can be totally made in deformable material (plastic material capable of being deformed and to return into its original shape once the deforming load is withdrawn) or can be partly made in rigid material (rigid plastics) and partly in deformable material having the above described properties. In detail the first and second lines 2, 3 have respective patient portions 2a, 3a, interposed between the patient and the deformable portion 15, and respective machine portions 2b, 3b interposed between the portion 15 and the first (or blood) chamber 1a of treatment unit 1. Going in further detail, the portion 15 presents a first port 5, connected or connectable by means of a connector piece with portion 2a of line 2, a second port 6, connected or connectable by means of a connector piece with portion 2b of line 2, a third port 7, connected or connectable by means of a connector piece with portion 3a of line 3, and a fourth port 8, connected or connectable by means of a connector piece with portion 3b of line 3. The first bloodline 2 and the second bloodline 3 are designed to be connected in use to a patient (not shown in the drawing tables).

Figure 6A:
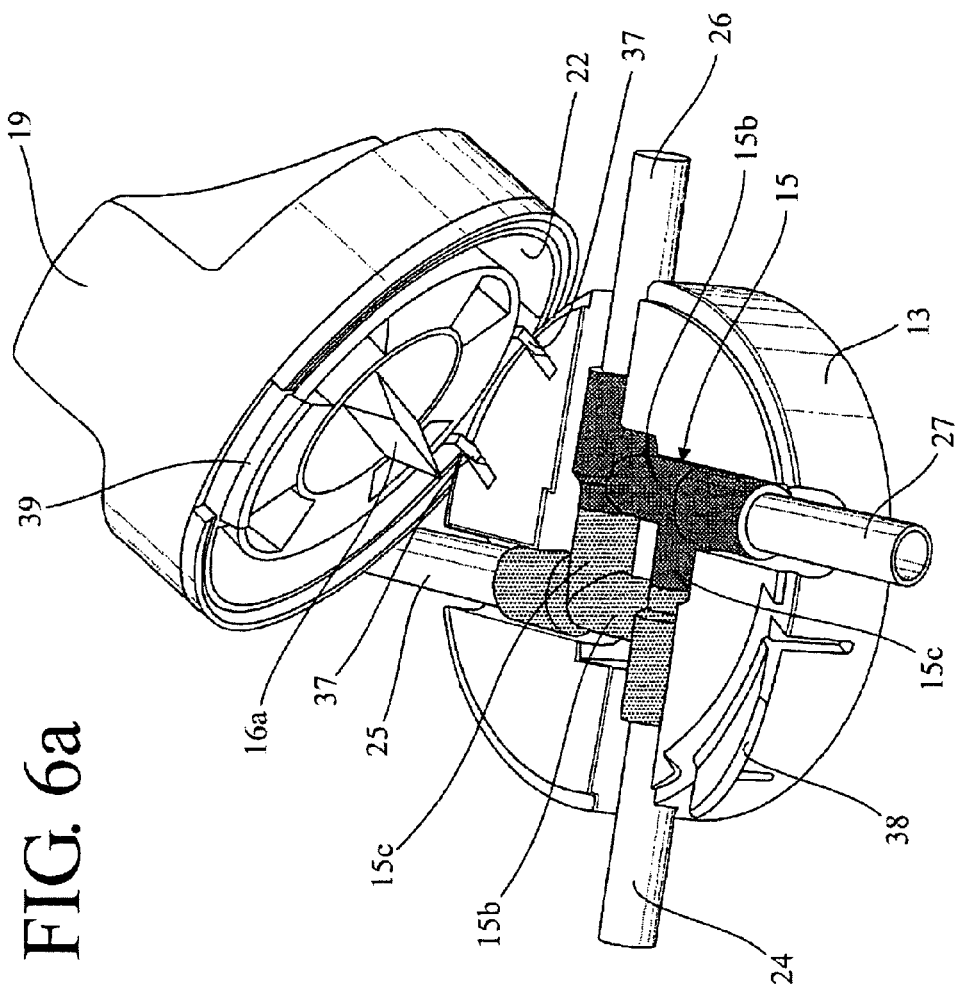
FIG. 6a is a perspective view, which shows the interior of a device according to an embodiment of the present invention.
Figure 6B:
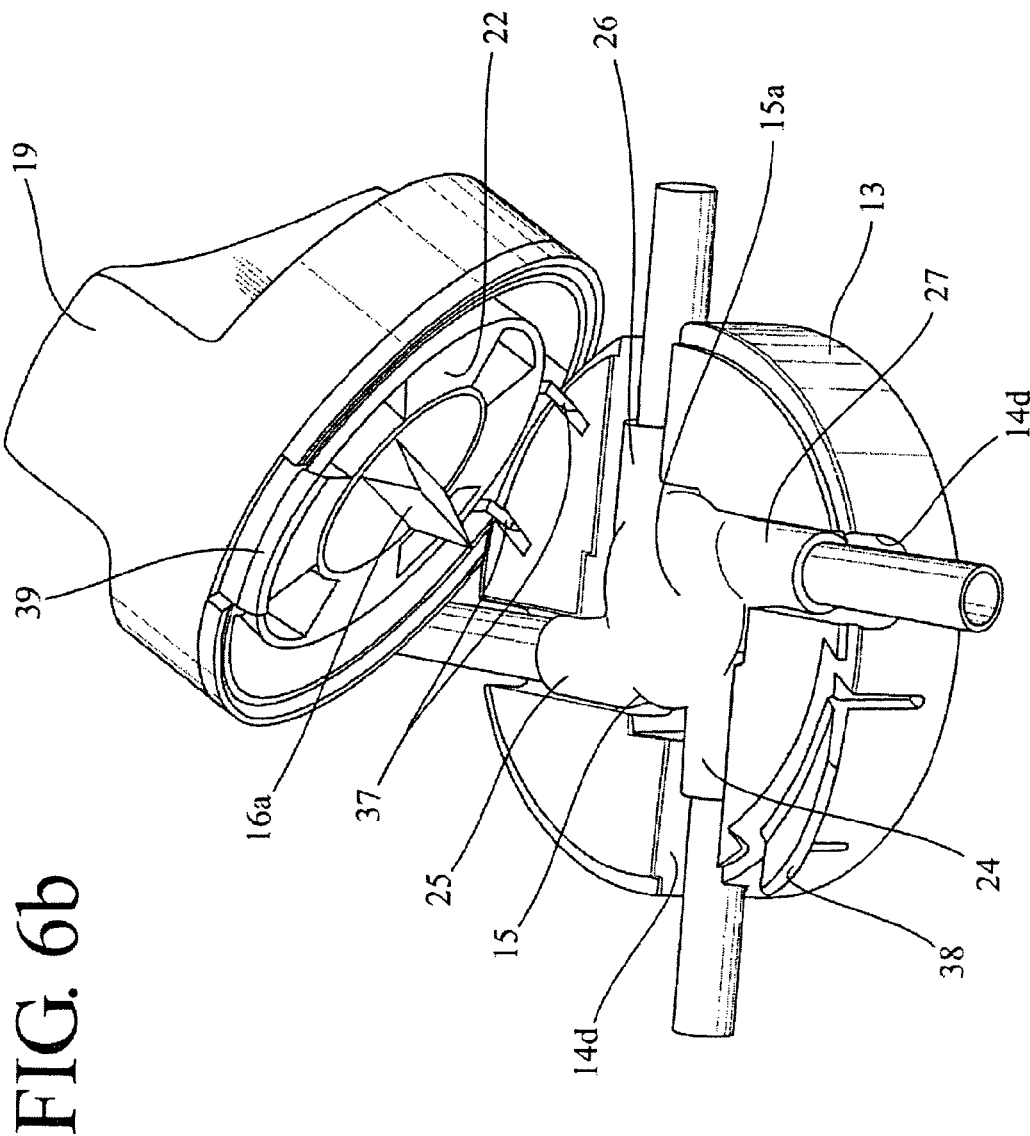
FIG. 6b is a perspective view, which shows the interior of a device according to another embodiment of the present invention.

In structural terms, the at least partly deformable portion 15 can comprise a common chamber 15a, which can be entirely deformable or which can comprise a rigid wall and a deformable opposite wall adapted for receiving the an active portion 16a of the switching device as it will be clarified here after; said first, second third, fourth ports are communicating with the common chamber and being adapted to be put on fluid communication with a corresponding respective portion of the two lines 2, 3 as above described (FIG. 6b).

Alternatively, use of a common chamber can be avoided by implementing a different solution as for instance shown in FIGS. 1, 2, 3a, 3b, 3c, 4, 6a where the portion 15 comprises an annular tubing presenting said four ports. Also in this case the annular tubing can be wholly deformable or being formed by a deformable wall structure and by a rigid wall structure integrally connected. In the embodiment shown the annular tubing is formed by a pair of first tubes 15b, and a pair of second tubes 15c transverse said first tubes. The four ports 5,6,7,8 are obtained in correspondence of intersections of the first tubes with the second tubes.

Again the deformable portion 15 can be obtained directly during manufacture of lines 2,3 and fixedly connected to said lines or, alternatively, the deformable portion 15 can be an independent component connectable to the lines 2,3 and/or to the treatment unit and/or to the vascular access by means of suitable connecting pieces.

As shown in the embodiment of FIG. 1, a pump 11, which pumps blood into the treatment unit in the direction denoted by the arrow 12, determines blood flow.

An apparatus 400 for controlling flow of fluid is operating on the bloodlines 2,3. The apparatus 400 includes a switching device 4 and the fluid distribution set deformable portion 15, which is arranged in the device 4. The switching device presents clamping means 16 (not shown in FIG. 1), for instance including an active portion 16a, such as a wedge or other suitable tool adapted for squeezing a deformable plastic material. The active portion 16a is adapted in use to deform and clamp the deformable portion 15 along two different lines denoted 9 and 10 in FIG. 1. With the active portion 16a positioned along the first dotted line 9, blood may flow from the first port 5 to the fourth port 8 and from the second port 6 to the third port 7. With the active portion positioned along the second dotted line 10, blood may flow from the third port 7 to the fourth port 8 and from the second port 6 to the first port 5. Thus, by changing the position of the active portion 16a with respect to the deformable portion 15 (along the first dotted line 9 or the second dotted line 10), blood flow in the bloodline portion 2a and in the bloodline portion 3b may be reversed, while keeping the same blood flow direction inside the first chamber 1a. As already mentioned portion 2a of bloodline 2 may be connected to a first section of a patient blood vessel, while the portion 3a of second blood line 3 may be connected to a second section downstream the first section of the same blood vessel so that, by virtue of the flow reversal, it is possible to withdraw blood from the downstream section thereby forcing access recirculation as required in some applications.

The switching device 4 also comprises a housing body 4a defining a seat 4b for receiving the deformable portion 15. As shown in the drawings the seat 4b is at least in part counter-shaped to the deformable portion in order to stably receive the same deformable portion 15. The clamping means 16 are coupled with the housing body 4a and, as already mentioned, can be positioned according to at least first and second clamping positions. In both said clamping positions, the active portion 16a is approached to a corresponding active surface 4c of the housing body in order to squeeze the deformable portion 15 according to line 9 or according to line 10 (again refer to FIG. 1).

More in detail, the housing body 4a comprises a first element 13 having a base wall 14a, defining at a least portion of said active surface, and a side wall 14b emerging from said base wall, laterally delimiting said seat and defining an access 14c for positioning of the deformable portion 15. In the drawings the base is indeed a bottom base and the positioning access extends over the bottom base. The sidewall of the first element presents radial passages 14d (please refer to FIGS. 6a, 6b) for seating conduit segments, which define the four ports of the deformable portion. The conduit segments can be lightly forced or snapped into said radial passages to secure a stable positioning of the portion 15.

Also the radial passages 14d present an open transverse section in order to define a positioning aperture for insertion of the deformable portion inside the seat, while laterally delimiting and keeping in place the four conduit segments or ports.

As shown in the drawing tables, the housing body also comprises a second element 22 coupled to the first element 13 and presenting a through aperture, the function of which will be further clarified herein below. The second element presents a wall, in the case shown being a top wall 22a, and a side wall 22b emerging from the top wall for partial closure of said seat 14c; the second element defines a zone facing the first element and adapted to host at least said active portion 16a in rest position, i.e. in a position where the active portion does not act on the deformable portion or acts on the deformable portion in a way not to define fluid flow barriers.

In the embodiments shown the first and the second element 13 and 22 present an overall cylindrical shape and are coaxially coupled. In the embodiments shown the through aperture 22c results in a center position of the top wall and is substantially coaxial to the deformable portion 15 and to the seat 14c. The second element of the housing body is hinged to the first element for instance in correspondence of a peripheral edge pivot. The second element can be shifted between an open condition (FIG. 6b), where the deformable portion can be seated in the corresponding seat, and a closed condition, where the second element is fixed to the first element and avoids extraction of the deformable portion 15. More in detail, hinges 37 arranged in correspondence of peripheral portion of the device 4, while at an opposite position lock 38 is provided on the first element; lock 38 is arranged to interact with a counterpart 39 on the second element and to lock each other the first and the second element 13 and 22.

Returning now to a more detailed description of the clamping means 16, said means comprises at least an axle 17 carrying the active portion 16a, and axially guided through the aperture 22c present on the top wall of the second element. The axle cooperates with means for urging the active portion 16a towards the deformable portion 15 or against the deformable part of portion 15 so that, absent other loads, the active portion is forced against the portion 15.

In order to control the action of the active portion, the clamping means shown in FIGS. 2, 3a, 3b, 3c, further comprises a knob 19 axially connected to the axle, and a flange 18 carried by the axle 17. As the axle passes through the aperture, then said second element 22 is axially interposed between the knob and the first element.

Figure 3A:
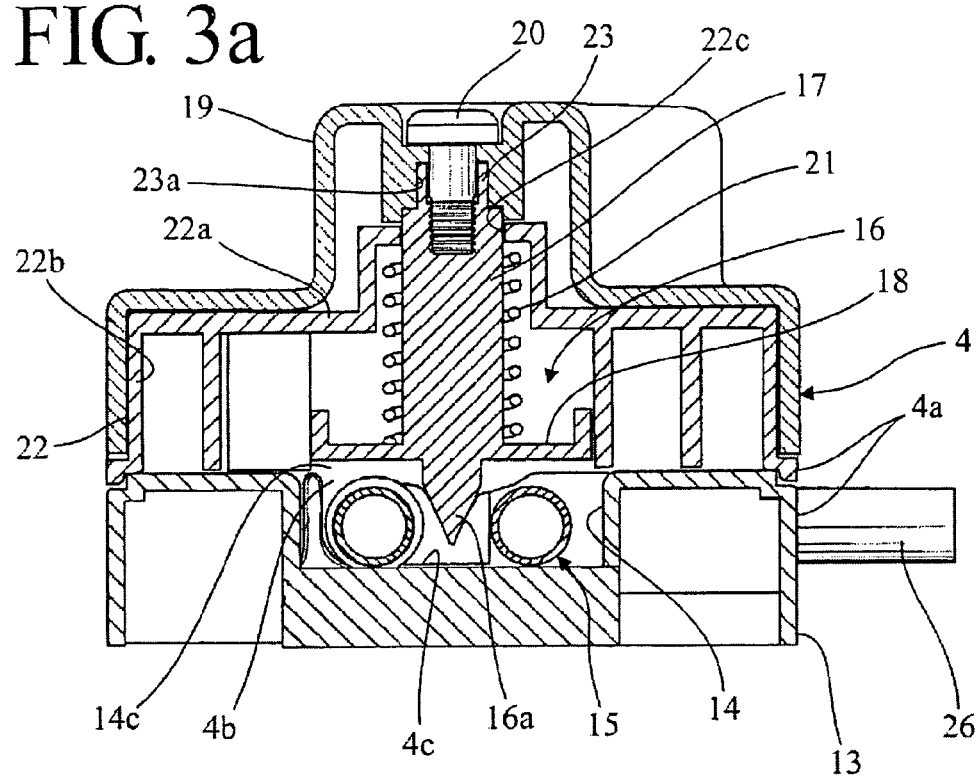
FIG. 3a is a cross section of a device as the one of FIG. 2, wherein clamp means is in position to deform the flow means.
Figure 3B:
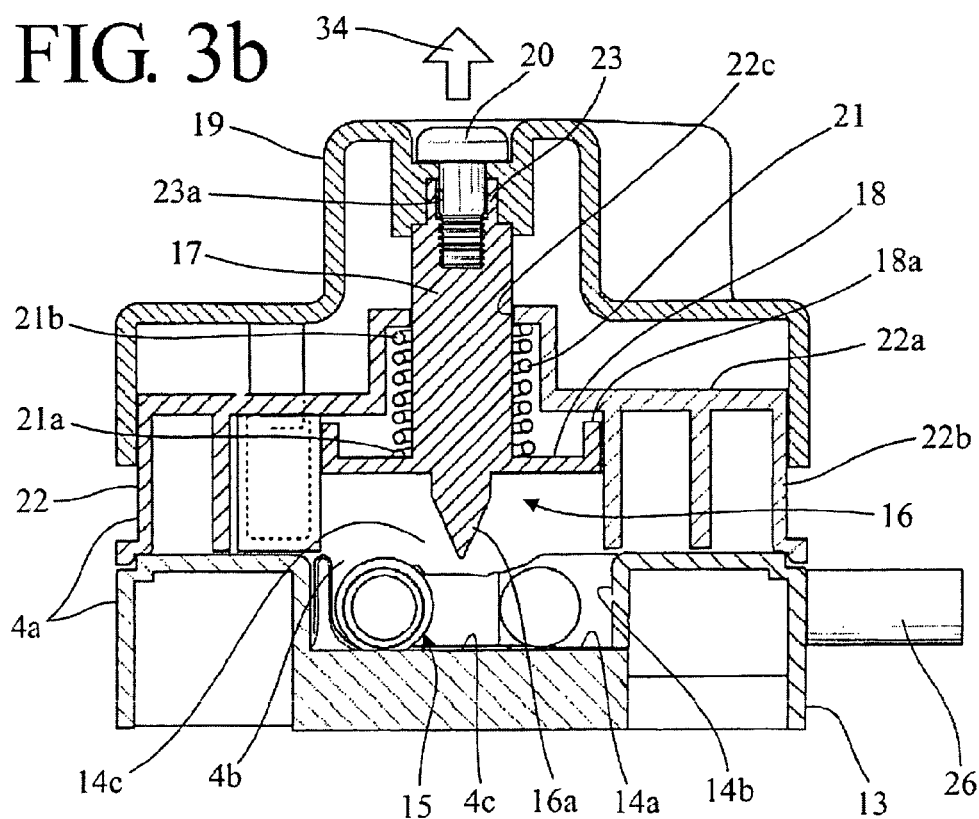
FIG. 3b is a cross section of a device as the one of FIG. 2 wherein clamp means is in position not to deform the flow means.
Figure 3C:
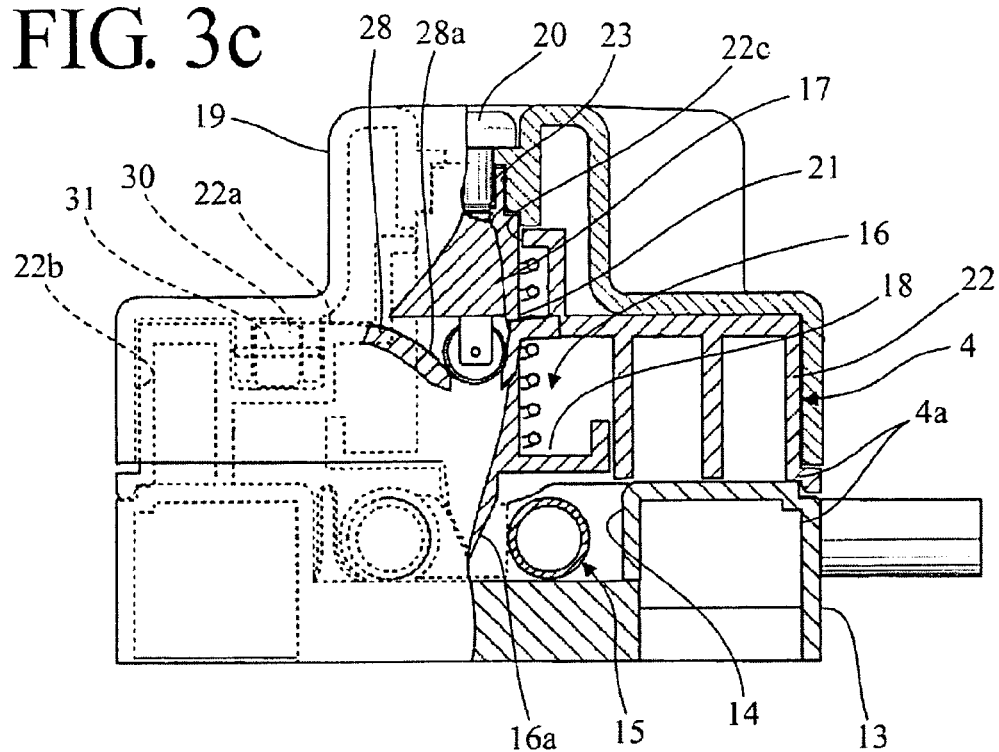
FIG. 3c is a cross section of a device as the one of FIG. 2 showing a track and a tracking means.

According to FIGS. 3a, 3b, 3c the urging means are arranged between the flange 18 and the second element 22 and tend to exert a force on the flange, which pushes the flange and active portion against the deformable portion 15.

Figure 4:
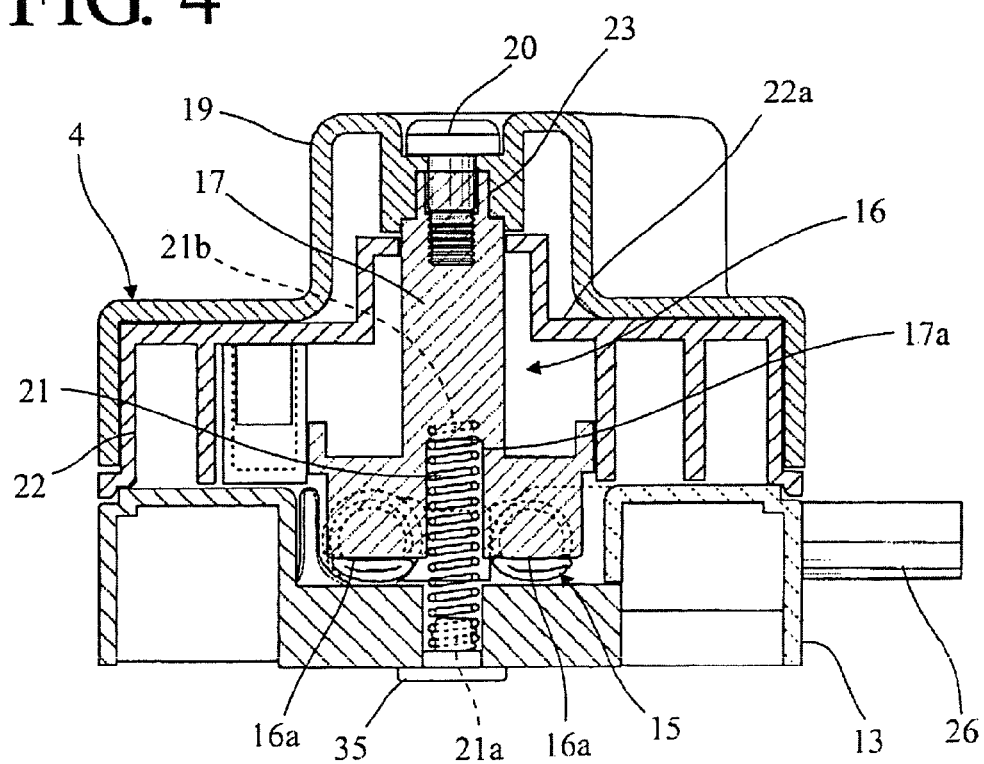
FIG. 4 shows a cross section of a different embodiment of the switching device according to the present invention.

Alternatively, as disclosed for instance in the embodiment of FIG. 4 the clamp means may comprise a terminal bore 17a carried by the axle 17. In this case the urging means can be arranged between said bore and the first element 13. In the embodiment of FIG. 4, the base of the first element includes a cap 35, which is movably coupled to the first element, and the urging means are arranged between said bore and the cap 35. The urging means in this case tend to pull the active portion 16a against the portion 15. The cap 35 can be used to have access to the urging means or even to regulate the attractive force exerted by the urging means.

The axle 17 is connected to the knob 19 by means of the square top 23 of the axle 17 being inserted into a square recess 23a in the knob 19. The knob is axially secured to the axle by means of a screw 20. The knob is rotatively engaged to the second element and is able to be axially lifted and lowered relative to said second element. In particular said flange presents an abutting surface designed 18a to define an axial stroke end against the wall 22a of the second element. Notice that while most of the drawings show a manual knob, which perhaps represents the cheapest way to control the clamping action of the clamping means, it could alternatively be used an automatic mechanism controlled by the equipment 100 and able to automatically impose the required displacements to the axle (see FIG. 7).

Going in further detail, the urging means may comprise at least a resilient element 21 (FIGS. 3a, 3b, 3c, 4), which could be at least a mechanic spring or pneumatic spring or a tubular band in natural or synthetic rubber, or other similar resilient body. In FIGS. 3a, 3b, 3c the spring 21 is coiled around axle 17 and has one end 21a acting against said flange and the other end 21b against an edge of the second element delimiting the aperture 22c. In FIG. 4 the spring is interposed between the cap 35 and the bore end 17a. Of course the spring end 21a could be directly engaged to the first element: however as already mentioned the solution shown in FIG. 4 results to be interesting because the cap 35, which is removably coupled to the first element, if removed allows easy separation of the first from the second element of the device. In the embodiment shown, the cap presents a threaded portion screwed to the first portion and allows for regulation of the spring preload pulling force and easy assembling/disassembling of the device.

Alternatively the urging means may include magnetic or electromagnetic couples (not shown). The magnetic or electromagnetic couples could comprise a main body (magnetic or magnetized or capable of being magnetized) fixed to said active portion or to a part rigidly connected to the active portion, and an auxiliary body (again magnetic or magnetized or capable of being magnetized) fixed to the first element. For instance in the embodiment of FIG. 4 the spring 21 could be substituted by a magnet fixed to the clamping means so as to be attracted by a counter magnet associated for instance to base wall of the first element.

Of course any other solution able to generate an urging force on the active portion could be used.

Notice again that, while the active portion is urged by the urging means against the portion 15, the clamping means can also be positioned according to a rest position. In said rest position, a distance of the active portion 16a from the corresponding active surface 4c in said clamping position is smaller than said distance in correspondence of the rest position.

As it will be explained in detail herein below, FIG. 3a shows the knob in one of the positions where the spring forces the wedge to deform the portion 15, while in FIG. 3b the knob 19 results in a position where the wedge 16a is spaced apart from the position of FIG. 3a and does not deform the portion 15.

The switching device also includes control means for allowing the clamping means to clamp the portion 15 in correspondence of prefixed clamping positions only. In detail, the control means comprises a guide profile 28, 29 carried by the housing body 4a, and at least a cursor member 30 adapted to follow the guide profile and mechanically connected to the active portion 16a so that an axial movement of the cursor following the shape of the guide determines a corresponding axial displacement of the active portion.

FIGS. 2, 3a, 3b, 3c, 4 show a case where the guide profile is carried by the second element and comprises a track including indents 28a, 29a directed versus said first element 13. In these embodiments the cursor member, for instance in the form of a wheel or a slide or a follower or other suitable means able to run inside tracks 28, 29 is carried by the said knob and runs in said track(s); the cursor 30 is positionable according to at least two functionally different positions: a first position wherein said cursor member is positioned in said indents and the urging means are able to move the active portion in one of the clamping positions, and a second position wherein the cursor member is positioned on said track outside the indents and the urging means are unable to move the active portion in clamping position.

Notice that the track may include at least two or more angularly spaced indents.

Referring to the embodiments of FIGS. 2, 3a, 3b and 3c, tracks 28 and 29 are arranged on the wall 22a of the second element 22 (in detail on the side of said wall facing away from the first element 13), and may include four angularly equally spaced indents; the knob carries two angularly opposite cursor members for defining two clamping positions angularly displaced for instance by 90°. In correspondence of said clamping positions the clamping means are designed for deforming the at least partially deformable portion 15 according to at least two respective clamp lines separated by 90 degrees from each other. Notice that the angular positions of indents, cursor members and active portion could be different from the one disclosed in detail.

Going now in further detail with reference to the embodiments of FIGS. 2, 3a, 3b, 3c, 4, the cursor member is a wheel 30, which is attached to the knob on an axle 31 and is arranged to run in the first track 28 and in the second track 29. Tracks 28 and 29 present at least one area where the sliding surface of the tracks defines said indents towards the first element. Therefore, when the wheel 30 reaches said indent (or indents if more then one, for instance positioned at the ends of the tracks 28, 29), the knob together with the clamping means is able to move towards the first element. The areas where the indents are located on tracks 28, 29 correspond to the wedge being positioned along the first dotted line 9 and the second dotted line 10 of FIG. 2. When the wheel reaches one of the indents, the knob, the wheel, the second element 22, the clamping means 16 is arranged to be forced by the spring to a lowered position where the wedge 16a is able to deform the flow means. By having the indents shaped with curved walls as is shown in the FIG. 3c the knob more easily turns into the position in which the wedge may deform the flow means.

In order to move the wedge from the position shown in FIG. 3a to the position shown in FIG. 3b the knob has to be lifted along arrow 34 of FIG. 3c and turned.

Figure 5:
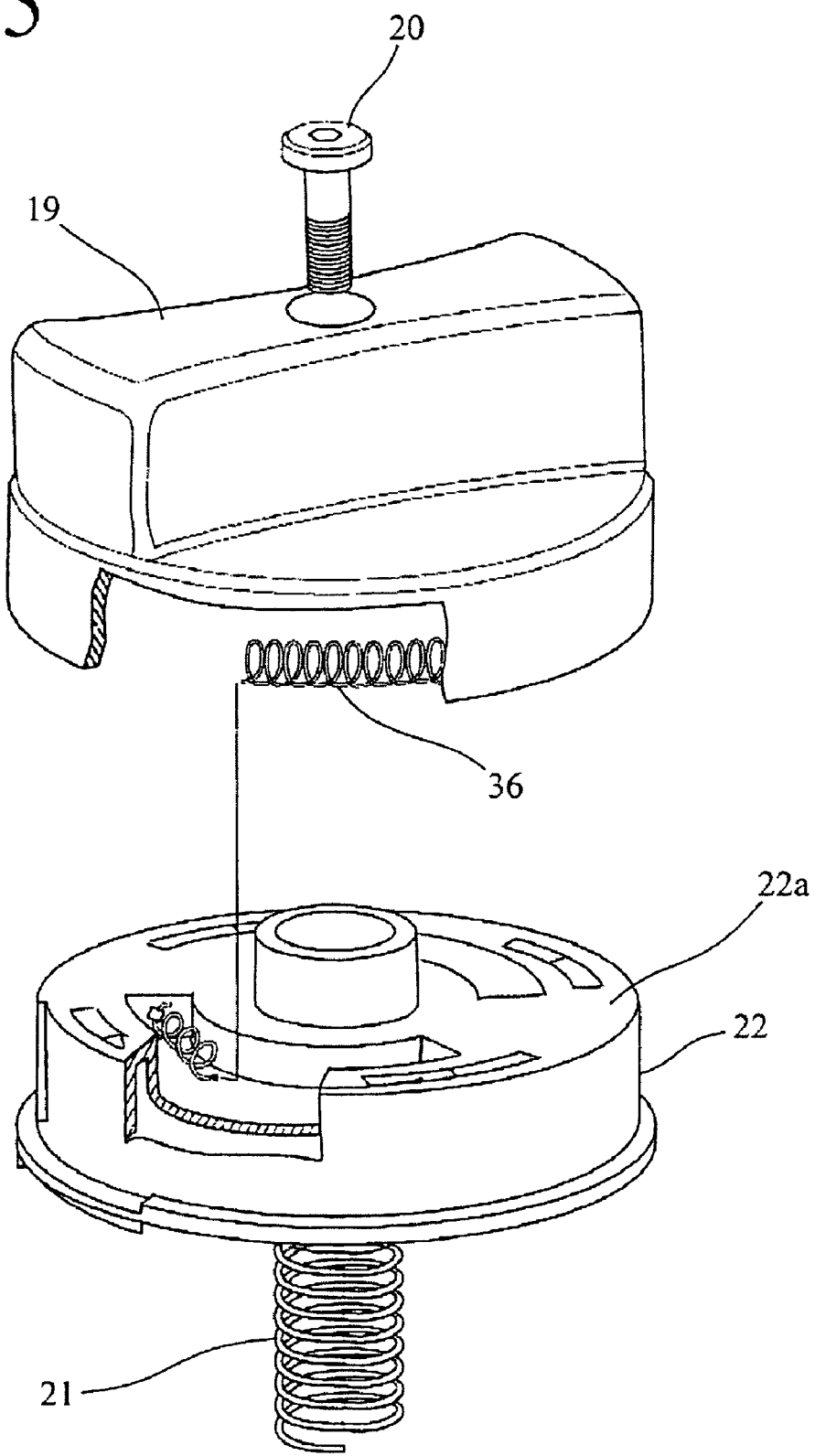
FIG. 5 shows a part of a device according to an embodiment of the present invention.

FIG. 5 shows a possible embodiment for the particular concerning the coupling between the knob 19 and the second element 22. Indeed the switching device can include return means 36 arranged between the clamping means and the second element 22. More in detail the return means is engaged between the knob and the second element to force the knob versus those clamping positions, in correspondence of which the clamping means are urged towards the portion 15. The return means comprises a resilient or a magnetic or an electromagnetic coupling arranged between the knob and the second element. Of course any suitable coupling capable of allowing relative movement between knob and second element while insuring a force urging the knob to assume at least one of the clamping positions could be used.

In operation, the knob is constantly forced to assume a preferred angular position with respect to the second element so that the wedge, by action of spring 21, will result in a preferred clamping condition towards the flow means. This arrangement is advantageous in cases where one of the clamping positions is preferred with respect to the other. This might be the case for example during hemodialysis when it is preferred that the blood lines are non-reversed, i.e. that the blood is taken from an upstream position and returned at a downstream position of a vascular segment.

Figure 7:
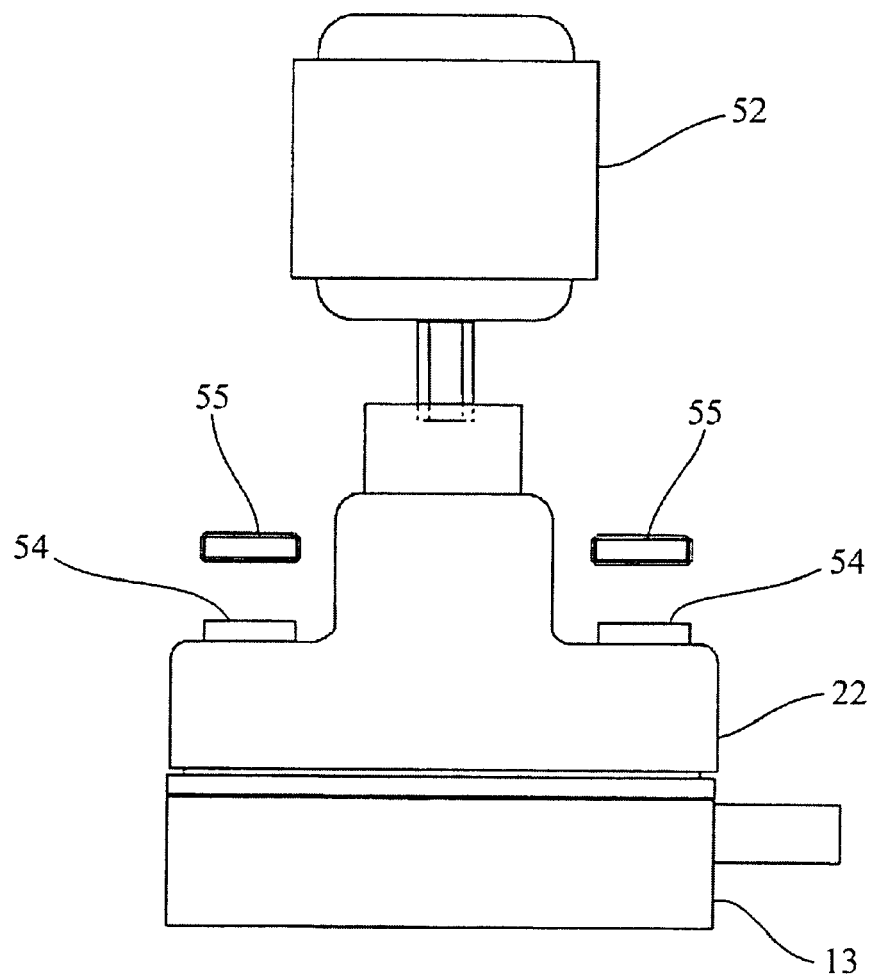
FIG. 7 shows schematically a device according to the present invention provided with a motor for controlling the switching of the device.

FIG. 7 shows schematically a device according to the present invention in which a motor 52 is arranged to turn the knob 53 or directly the axle 17. Of course the motor could in principle directly operate the active portion with no need of knob interposition. Further, there are arranged ferromagnetic metal pieces 54 on both sides of the knob. Electromagnets 55 are provided to attract the ferromagnetic pieces and thus also the knob to lift it from the position in which the clamp means is arranged to deform the flow means. Of course other automatic means for lifting the knob or directly the active portion could be devised, such as a pneumatic actuator, an electric actuator and so on. The device may be similar to the embodiment shown in FIG. 2. In operation the electromagnets attract the ferromagnetic pieces and thus also the knob and lifts it sufficiently to allow it to be turned. Then the motor rotates the knob to position it in another of the positions in which the clamp means may be positioned to clamp the flow means. In the new position the electromagnets release the knob and allows the clamp means to deform the flow means. Notice that as means are provided for automatically lifting the active portion (or the knob), said means could be operated also for lowering the active portions in correspondence of the desired angular positions (i.e. the clamping positions). In this case the means for lifting and lowering would be part of the clamping means with no need of any other mechanisms f9or controlling the movement of the active portion.

Figures 8A, 8B:
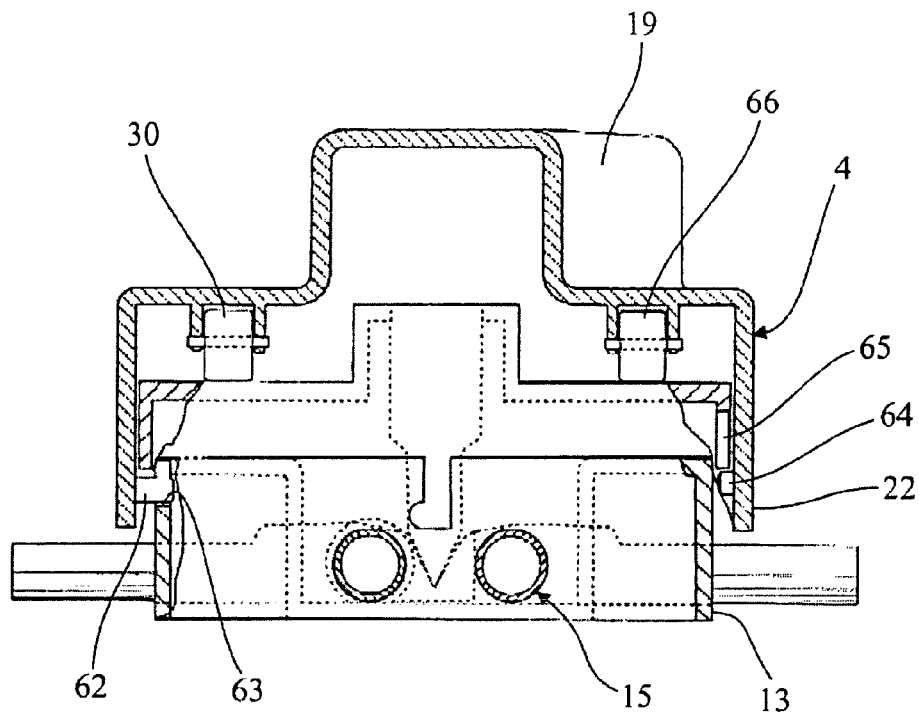
FIG. 8a shows an alternative embodiment of a device according to the present invention, wherein the clamp means is in position to deform the flow means.
FIG. 8b shows the embodiment of FIG. 8a, wherein the clamp means is in position to be turned.

FIGS. 8a and 8b show a device according to an alternative embodiment of the present invention. The main difference between this embodiment and the embodiments of FIGS. 2, 3a, 3b, 3c, 4 described above is that it does not have any resilient means forcing the clamp means against the flow means. Instead the clamp means is forced towards the first element by urging means, which include a bayonet joint.

FIG. 8a shows a cross section of the device. The first element 13 has a seat 4b in which the deformable portion is arranged. Differently from the other embodiments the second element 22 is arranged movable in relation to the first 13. The second element rigidly carries the clamping means, comprising the active portion 16a. Knob 19 is arranged movable in relation to both the first element and the second element. The knob 19 has a first set of taps 62 which are arranged to move in a first set of tracks 63 on the first element 13. The first set of taps 62 and the first set of tracks 63 together form a bayonet joint. The knob also has a second set of taps 64 which are arranged to interact with a second set of tracks 65. The knob also comprises a number of wheels 66 which are arranged to roll on the surface of the second element facing the knob. The first set of tracks 63 allows the second element with the wedge to be moved towards the first element only in a few different positions. The second set of taps and the second set of tracks are arranged to interact with each other only when the first set of taps has been lifted from its bottom positions in the first set of tracks 63.

In operation when the first set of taps are in their bottom positions in the first set of tracks, the wheels 66 are in contact with the top surface of the second element facing the knob 19 and the wheels 66 presses the wedge or active portion 16a towards the deformable portion 15 and deforms the same. In the lowermost position the knob 19 may be turned in relation to the first element and the second element to a secured position wherein the first set of taps 62 are in the end of the first set of tracks. During the rotation of the knob in relation to the second element 22, the wheels 66 (other low friction means could be equivalently used) provide low friction between the knob 19 and the second element 22. By turning the knob 19 in the other direction the first set of taps are released and the knob 19 may be lifted in relation to the first element 13. During this movement the second set of taps 64 starts to interact with the second set of tracks 65 in the second element 22 and the second element will be lifted together with the knob 19. In the position shown in FIG. 8b the knob 19 is connected to the second element 60 by means of the second set of taps 64 and the second set of tracks 65, and the knob 19 and the second element 60 may be rotated in relation to the first element 13.

The embodiments described above may be modified in a number of ways obvious to the man skilled in the art without departing from the scope and the spirit of the invention, which is defined by the appending claims.

The invention claimed is:

1. Switching device for a fluid distribution set, said set presenting an at least partially deformable portion having a first port, a second port, a third port and a fourth port, the switching device comprising:
    clamping means having at least an active portion adapted, in use, for clamping said at least partially deformable portion of the fluid distribution set,
    a housing body defining a seat for receiving said at least partially deformable portion, the clamping means being coupled with the housing body and being positionable according to at least a first and a second clamping positions, wherein the active portion is positioned near a corresponding active surface of the same housing body.

2. Device according to claim 1, wherein said housing body comprises a first element having a base wall, defining at least a portion of said active surface, and a side wall emerging from said base wall, laterally delimiting said seat and defining an access for positioning of the at least partially deformable portion.

3. Device according to claim 2, wherein the sidewall of the first element presents radial passages for seating conduit segments defining said ports of the at least partially deformable portion.

4. Device according to claim 3, further comprising a second element movably coupled to the first element, the second element rigidly carrying the clamping means.

5. Device according to claim 4, further comprising urging means for forcing said active portion towards the first element, the urging means including a knob acting on the second element and at least one bayonet joint coupling between the knob and the first element.

6. Device according to claim 2, wherein the clamping means comprises:
    at least an axle carrying the active portion, and means, active on the axle, for urging the active portion towards the at least partially deformable portion.

7. Device according to claim 6, further comprising a second element coupled to the first element and presenting a through aperture for axially guiding at least a portion of the axle.

8. Device according to claim 7, wherein the clamping means further comprises a knob axially connected to the axle, and a flange carried by the axle, said second element being axially interposed between the knob and the first element, said urging means being arranged between the flange and the second element.

9. Device according to claim 8, wherein the clamping means further comprises a terminal bore carried by the axle, said urging means being arranged between said bore and the first element.

10. Device according to claim 9, wherein the base of the first element includes a cap, said cap being movably coupled to the first element, and wherein the clamping means further comprises a terminal bore carried by the axle, said urging means being arranged between said bore and the cap.

11. Device according to claim 6, wherein the urging means comprises an automatic actuator able to move back and forth according to a prefixed direction of said axle.

12. Device according to claim 11, further comprising a second element coupled to the first element and presenting a through aperture for axially guiding at least a portion of the axle.

13. Device according to any one of claims 7, or 11, wherein the second element comprises a top wall and a side wall emerging from the top wall for partial closure of said seat, the second element defining at least a zone facing the first element and adapted to host at least said active portion in a rest position.

14. Device according to claim 7 or 9, wherein the second element is fixable to the first element.

15. Device according to claim 8 or 9, wherein the axle is rotatively engaged to the housing and is able to be axially lifted and lowered relative to said second element.

16. Device according to claim 8 or 9, wherein the knob is rotatively engaged to the second element and is able to be axially lifted and lowered relative to said second element, said flange presenting an abutting surface designed to define an axial stroke end against the wall of the second element.

17. Device according to claim 15, wherein the clamping means include an actuator connected the axle to axially lift and lower said axle relative to said second element and/or to turn the axle around its longitudinal axis to thereby achieve an angular displacement of the active portion.

18. Device according to claim 6, wherein the urging means comprises at least a resilient element.

19. Device according to claim 6, wherein the urging means comprises magnetic or electromagnetic couples.

20. Device according to claim 19, wherein the magnetic or electromagnetic couples comprise a main body fixed relative to said active portion, said main body being magnetic or magnetized or capable of being magnetized, and an auxiliary body fixed relative to the first element, said auxiliary body being magnetic or magnetized or capable of being magnetized.

21. Device according to claim 1, wherein the clamping means can also be positioned according to a rest position, a distance of the active portion from the corresponding active surface of the receiving means in said clamping position being smaller than said distance in correspondence of the rest position.

22. Device according to claim 1, comprising control means for allowing the clamp means to clamp the at least partially deformable portion in prefixed clamping positions only.

23. Device according to claim 22, wherein the control means comprises:
a guide profile carried by the housing body, at least a cursor member adapted to follow the guide profile and mechanically connected to the active portion.

24. Device according to claim 23, wherein the guide profile is carried by the second element and comprises a track and indents directed towards said first portion.

25. Device according to claim 24, wherein the cursor member runs in the track, said cursor member being carried by the knob and being positionable according to at least two functionally different clamping positions, wherein said cursor member is positioned in one of said indents and the urging means are able to move the active portion in one of the clamping positions, and one or more rest positions wherein the cursor member is positioned on said track outside the indents and the urging means are unable to move the active portion in a clamping position.

26. Device according to claim 25, wherein the guide profile includes at least two angularly spaced indents.

27. Device according to claim 25, wherein said guide profile is formed on the top surface of said second element facing said knob, said profile including four angularly equally spaced indents and the knob carrying two angularly opposite cursor members for defining two clamping positions, said clamping positions corresponding to the clamping means, said clamping means being designed to deform the at least partially deformable portion according to at least respective clamp lines separated by 90 degrees from each other.

28. Device according to claim 22, wherein return means is arranged between the clamping means and the second element to force the clamping means towards one of said clamping positions.

29. Device according to claim 28, wherein the return means comprises a resilient or a magnetic or an electromagnetic coupling arranged between the knob and the second element.

30. Device according to claim 1, wherein the clamping means is positionable in two positions only.

31. Fluid control apparatus comprising a switching device according to claim 1, said apparatus also comprising an at least partially deformable portion of a fluid distribution set, said at least partially deformable portion having a first port, a second port, a third port and a fourth port.

32. Fluid control apparatus according to claim 31, wherein the at least partially deformable portion is adapted to be put in fluid communication with a venous tube and an arterial tube of the distribution set by means of said ports.

33. Fluid control apparatus according to claim 32, wherein the at least partially deformable portion comprises a common chamber and said first, second third, and fourth ports communicating with the common chamber and being adapted to be put in fluid communication with a corresponding respective portion of the venous line or the arterial line.

34. Fluid control apparatus according to claim 32, wherein the at least partially deformable portion comprises an annular tubing presenting said four ports.

35. Fluid control apparatus according to claim 34, wherein the annular tubing comprises:
a pair of first tubes, and
a pair of second tubes transverse to said first tubes.

36. Fluid control apparatus according to claim 31, wherein the active portion corresponding to said clamping positions is active on the at least partially deformable portion so that flow either is precluded from the first and third ports and redirected to the second and fourth ports, or precluded from the first and fourth ports and redirected to the second and third ports.

37. Fluid control apparatus according to claim 36, wherein the active portion in said clamping positions is arranged to clamp over a clamp area and to clamp over the entire clamp area substantially simultaneously.

38. Fluid control apparatus according to claim 31, wherein the conduit segments can be lightly forced or snapped into said radial passages to secure a stable positioning of the at least partially deformable portion.

39. Blood treatment equipment comprising:
a fluid control apparatus according to claim 31, and
a fluid distribution set, said fluid distribution set having a blood treatment unit having a first and a second chamber separated by a semipermeable membrane, and first and second lines connected to the treatment unit first chamber and to the at least partially deformable portion.

* * * * *

UNITED STATES PATENT AND TRADEMARK OFFICE
CERTIFICATE OF CORRECTION

| | | |
|---|---|---|
| PATENT NO. | : 7,836,914 B2 | Page 1 of 1 |
| APPLICATION NO. | : 11/008195 | |
| DATED | : November 23, 2010 | |
| INVENTOR(S) | : Johan Drott et al. | |

It is certified that error appears in the above-identified patent and that said Letters Patent is hereby corrected as shown below:

In claim 13, column 13, line 1, "any one of claims 7, or 11," should read
--any one of claims 7, 11, or 4,--.

In claim 14, column 13, line 7, "claim 7 or 9," should read --claim 7 or 11,--.

In claim 15, column 13, line 9, "claim 8 or 9," should read --claim 8 or 11,--.

In claim 16, column 13, line 12, "claim 8 or 9," should read --claim 8 or 11,--.

In claim 17, column 13, line 18, "means include an actuator connected the axle" should read --means includes an actuator connected to the axle--.

In claim 25, column 13, line 56, "means are able" should read --means is able--.

In claim 25, column 13, line 59, "means are unable" should read --means is unable--.

In claim 33, column 14, line 30, "second third," should read --second, third,--.

Signed and Sealed this
Twenty-second Day of March, 2011

David J. Kappos
*Director of the United States Patent and Trademark Office*